(12) United States Patent
Harberts et al.

(10) Patent No.: US 8,948,843 B2
(45) Date of Patent: Feb. 3, 2015

(54) PROBE FOR AN IMPLANTABLE MEDICAL DEVICE

(75) Inventors: Dirk Willem Harberts, Eindhoven (NL); Ke Wang, Eindhoven (NL); Michel Marcel Jose Decre, Eindhoven (NL)

(73) Assignee: Sapiens Steering Brain Stimulation B.V., Eindhoven (NL)

( * ) Notice: Subject to any disclaimer, the term of this patent is extended or adjusted under 35 U.S.C. 154(b) by 175 days.

(21) Appl. No.: 13/120,854

(22) PCT Filed: Oct. 8, 2009

(86) PCT No.: PCT/IB2009/054401
§ 371 (c)(1),
(2), (4) Date: Mar. 24, 2011

(87) PCT Pub. No.: WO2010/044019
PCT Pub. Date: Apr. 22, 2010

(65) Prior Publication Data
US 2011/0190860 A1  Aug. 4, 2011

(30) Foreign Application Priority Data
Oct. 15, 2008  (EP) .................................... 08166662

(51) Int. Cl.
*A61B 5/055* (2006.01)
*A61N 1/08* (2006.01)
(Continued)

(52) U.S. Cl.
CPC ............. *A61N 1/0534* (2013.01); *A61B 5/6864* (2013.01); *A61N 1/0529* (2013.01); *A61B 5/6865* (2013.01); *A61B 5/0476* (2013.01); *A61B 19/201* (2013.01); *A61N 2001/086* (2013.01)
USPC ............................ 600/420; 600/423; 600/424

(58) Field of Classification Search
USPC ............................................... 607/9, 63, 121
See application file for complete search history.

(56) References Cited

U.S. PATENT DOCUMENTS

| 4,352,360 A | 10/1982 | King |
| 6,496,714 B1 | 12/2002 | Weiss |

(Continued)

FOREIGN PATENT DOCUMENTS

| EP | 1488738 A1 | 12/2004 |
| JP | 2005-515854 A | 2/2005 |

(Continued)

OTHER PUBLICATIONS

Lemieux, Louis et al "Recording of EEG During FMRI Experiments: Patient Safety" Magnetic Resonance in Medicine, vol. 38, No. 6, Dec. 1997, pp. 943-052.

(Continued)

*Primary Examiner* — Carl H Layno
*Assistant Examiner* — Jon Eric C Morales
(74) *Attorney, Agent, or Firm* — Shumaker & Sieffert, P.A.

(57) ABSTRACT

The invention relates to a probe (10) for an implantable medical device. The probe has a distal end (2) and a proximal end (3), and the probe (10) moreover comprises an electrode (1) at the distal end. The electrode is connected to a wire (5) extending from the electrode to the proximal end of the probe, where the resistivity of the wire is non-uniform along the length of the wire. The wire may have high resistivity at the distal end of the probe and low resistivity wires elsewhere. The high resistivity wires reduce the peak current density in the tissue of an implanted device, and thus prevents destructive heating and/or undesired stimulation of tissue during MRI examination. This highly contributes to MR safety which is a highly desired feature for these implantable electrical stimulation devices.

13 Claims, 5 Drawing Sheets

(51) Int. Cl.
*A61N 1/05* (2006.01)
*A61B 5/00* (2006.01)
*A61B 5/0476* (2006.01)
*A61B 19/00* (2006.01)

(56) References Cited

U.S. PATENT DOCUMENTS

| | | | |
|---|---|---|---|
| 6,720,497 | B1 | 4/2004 | Barsne |
| 2006/0009819 | A1 | 1/2006 | Przybyszewski |
| 2006/0252314 | A1 | 11/2006 | Atalar |
| 2008/0033497 | A1 | 2/2008 | Bulkes |
| 2009/0118610 | A1* | 5/2009 | Karmarkar et al. ........... 600/420 |

FOREIGN PATENT DOCUMENTS

| WO | 02074164 A1 | 9/2002 |
|---|---|---|
| WO | 2006121469 A1 | 11/2006 |
| WO | 2007047966 A2 | 4/2007 |
| WO | 2007/064739 A3 | 6/2007 |
| WO | 2007064739 A2 | 6/2007 |
| WO | 2008024346 A2 | 2/2008 |
| WO | 2008032249 A2 | 3/2008 |

OTHER PUBLICATIONS

Bonmassar, Giorgio "Resistive Tapered Stripline (RTS) in Electroencephalogram Recordings during MRI", IEEE Transactions on Microwave Theory and Techniques, vol. 52, No. 8, Aug. 2004, pp. 1992-1998.

Notice of Reason for Rejection mailed Oct. 8, 2013 for Japanese Patent Application No. 2011-531593.

Office Action issued by Chinese Patent Office dated Jan. 13, 2014 for Chinese Patent Application No. 200980140967.7.

Giorgio Bonmassar, "Resistive Tapered Stripline (RTS) in Eletroencephalogram Recordings During MRI"—IEEE Transactions on Microwave Theory and Techniques, vol. 52, No. 8, Aug. 2004.

Notice of Reasons for Rejection dated May 13, 2014 for Japanese Patent Application No. 2011-531593.

* cited by examiner

PROBE FOR AN IMPLANTABLE MEDICAL DEVICE

FIELD OF THE INVENTION

The present invention relates to a probe for an implantable medical device, in particular a probe for a brain implantable medical device.

BACKGROUND OF THE INVENTION

Implantable medical devices are commonly used today to treat patients suffering from various ailments. After implant of an implantable device for electric stimulation, such as pacemakers or Deep Brain Stimulation (DBS) devices, the device and surrounding tissue may be heated during scanning of the patient and device by e.g. Magnetic Resonance Imaging (MRI) scanning. The human tissue, in particular brain tissue, is sensitive to temperature raises; the maximum allowed temperature increase of brain tissue is 1° C. in that further temperature increases may have profound, negative effects on single neuron and neuronal network function. Therefore it is of concern to minimize heating effects at and around an implanted medical device due to induced currents near the medical device during MRI scanning.

It might seem natural to choose high resistive materials throughout the implantable device, ideally with the same specific resistance as the human tissue. However, this typically would require much more power to obtain the same tissue stimulating signals at the end of the probe compared to probes using low resistive materials. Consequently, either unacceptable large batteries or unacceptable short battery life time would result.

U.S. Pat. No. 4,353,360 describes an electrode for a body implantable lead having a semiconductor surface for coupling of electrical signals to the body tissue. The electrode comprises several materials of differing conductivities, arranged in layers such that the material having the lowest conductivity is in direct contact with the body tissue.

An improved probe for implantable medical devices with minimized heating effect would be advantageous. Moreover, a probe which after implant and during MRI scanning would produce a reduced current density within the human tissue surrounding the probe of the implanted device, compared to known probes for implantable medical devices, would be advantageous.

SUMMARY OF THE INVENTION

It may be seen as an object of the present invention to provide an alternative probe for implantable medical devices that avoids the above mentioned problems with regard to heating and/or large current densities.

This object and several other objects are obtained in a first aspect of the invention by providing a probe for an implantable medical device, said probe having a distal end and a proximal end, said probe moreover comprising an electrode at the distal end, where said electrode is connected to a wire extending from the electrode to the proximal end of the probe, wherein the resistivity of the wire is non-uniform along the length of the wire.

By providing a probe having electrodes connected to wire, where the wire has non-uniform resistivity, it is possible to customize the probe so that the issues of security with relation to preventing unwanted heating during MRI scanning, and battery life time may be balanced against each other.

The invention is particularly, but not exclusively, advantageous for reducing high current densities and thus heating of the probe of the implantable medical device and/or the tissue surrounding it when the device is implanted in a patient. In order to prevent destructive heating or undesired stimulation of the human tissue due to induced currents near the ends of electrodes during MR scanning, a high resistivity of the wires in the probe is required. This conflicts with the need for low power consumption to increase battery lifetime, because for this a low resistance of the signal wires is required. The non-uniform resistivity of the wire provides a solution wherein some parts of the wire from an electrode to the proximal end of the probe has a lower resistivity, which is advantageous to the battery lifetime, and other parts of the wire are of a higher resistivity, which reduces the heating and undesired stimulation of human tissue around the probe.

In the case of a plurality of electrodes at the distal end of the probe connected by wires to the proximal end of the probe, the advantageous effect of the non-uniform resistivity of wires connecting each electrode to the distal end of the probe is of course increased, when the fraction of the wires having non-uniform resistivity along the length of the probe is increased; however, the advantageous effect may be achieved even if only one out off a plurality of wires extending along the probe has non-uniform resistivity.

According to an aspect of the implantable medical, the wire comprises a first section having a first resistivity and a second section having a second resistivity, said first and second resistivities being different. The term "section" is meant to denote a part along the length of the wire; throughout this application the first section is closer to the distal end than the second section.

According to another aspect of the probe, the first section of the wire is contiguous to the electrode and the resistivity of the first section is higher than the resistivity at the second section. When the resistivity of the first section of wire close to or at the electrode is high, the current density around the electrode during an external electric field may be reduced. Thus, the current density at the human tissue, when the probe is implanted, will be reduced.

In the tissue surrounding an implanted medical device, the currents typically concentrate near the distal end of the probe, when the patient and the probe are in an MRI field. This causes heating of both the tissue and the probe. The invension proposes to increase the resistivity of the wire where the current density otherwise would be the largest, so that the current will spread out more. Typically, this will also reduce the total induced current at MRI frequency, but even if the total current would remain the same, the heating would reduce due to the more uniform distribution of current around the implanted probe, since the heating is proportional to the square of the current density.

According to yet another aspect, the first section is made of material of a first resistivity and the second section is made of material of a second resistivity, where the first resistivity is higher than the second resistivity. Alternatively or concurrently, the first section of the wire has a first sectional area and the second section of the wire has a second sectional area, where the first sectional area is smaller than the second sectional area. According to the latter aspect, the sectional area of the wire is non-uniform along the length of the probe. Thus, the variation in resistivity can be achieved by varying the resistivity of the material and/or varying the sectional area or the thickness of the wire.

According to a further aspect, the second section of the wire is longer than the first section of the wire. Thus, the major part of the wire has low resistivity and the remainder of the wire is of higher resistivity. For example, the first section of the wire may constitute between 2% and 40%, preferably between 5% and 20%, more preferably about 10% and 15% of the wire. The term "longer" as used here is meant to denote "larger in the longitudinal direction of the wire". The longitudinal direction of the wire typically corresponds to the longitudinal direction of the probe.

The resistivity of the first section may be 2 to 10 times higher than the resistivity of the second section. Hereby, a more uniform distribution of the current along the entire probe may be achieved compared to probes having electrodes connected by wires with uniform resistivities.

According to yet a further aspect, the first section of the wire is of polysilicon material and the second section of the wire is of metallic material. Polysilicon material is high-ohmic, resulting in lower current density at the first section of the wire.

According to another aspect of the probe, the wire comprises one or more further sections, each further section having a resistivity different from other sections of the wire. Thus, the wire may comprise a plurality of resistivities. Alternatively, the resistivity of the wire changes continuously along the length of the wire. Adjacent sections of wire having different resistivity may create hotspots of relatively high current density, when the probe is in an external electromagnetic field. By providing a wire with a continuous change in resistivity, such hotspots may be alleviated.

The different aspects of the present invention may each be combined with any of the other aspects. These and other aspects of the invention will be apparent from and elucidated with reference to the embodiments described hereinafter.

BRIEF DESCRIPTION OF THE FIGURES

The present invention will now be explained, by way of example only, with reference to the accompanying Figures, where.

DETAILED DESCRIPTION OF AN EMBODIMENT

Figure 1:
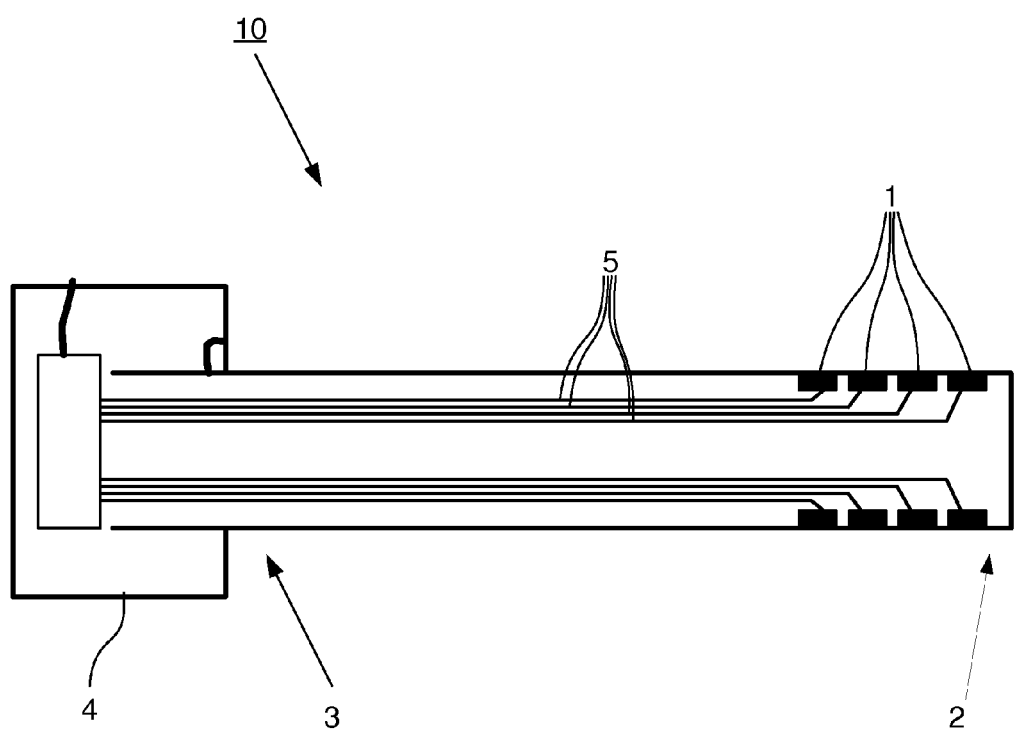
FIG. 1 is a cross section of a probe for implantable electro-stimulation devices.

FIG. 1 is a cross sectional view of an electro-stimulation probe 10 according to an embodiment of the invention. The probe 10 has a distal end 2 and a proximal end 3. The probe 10 has a plurality of electrodes 1 situated close to the distal 2 end thereof. Alternatively, only one electrode 1 would be conceivable; however in order to provide high resolution stimulation, more than one electrode is advantageous. FIG. 1 moreover illustrates a chamber 4 housing electronics and connected to the proximal end 3 of the probe 10. Moreover, FIG. 1 discloses wires 5 extending from each of the electrodes 1 to the proximal end 3 of the probe 10 and to the chamber 4.

The probe is arranged for being implanted into the tissue of a patient to be treated, such as in the spinal cord, nerve roots, muscles, or brain tissue, in order to provide electrical stimulation of such a region of interest, the stimulation of which is expected to alleviate a condition of the patient. The electro-stimulation device typically comprises a battery (not shown) and a pulse generator (not shown) connected to the proximal end 3 of the probe 10 via the chamber 4 for generation of patterns of electric pulses that stimulate the tissue, via the electrodes 1 of the probe 10.

Figure 2A:
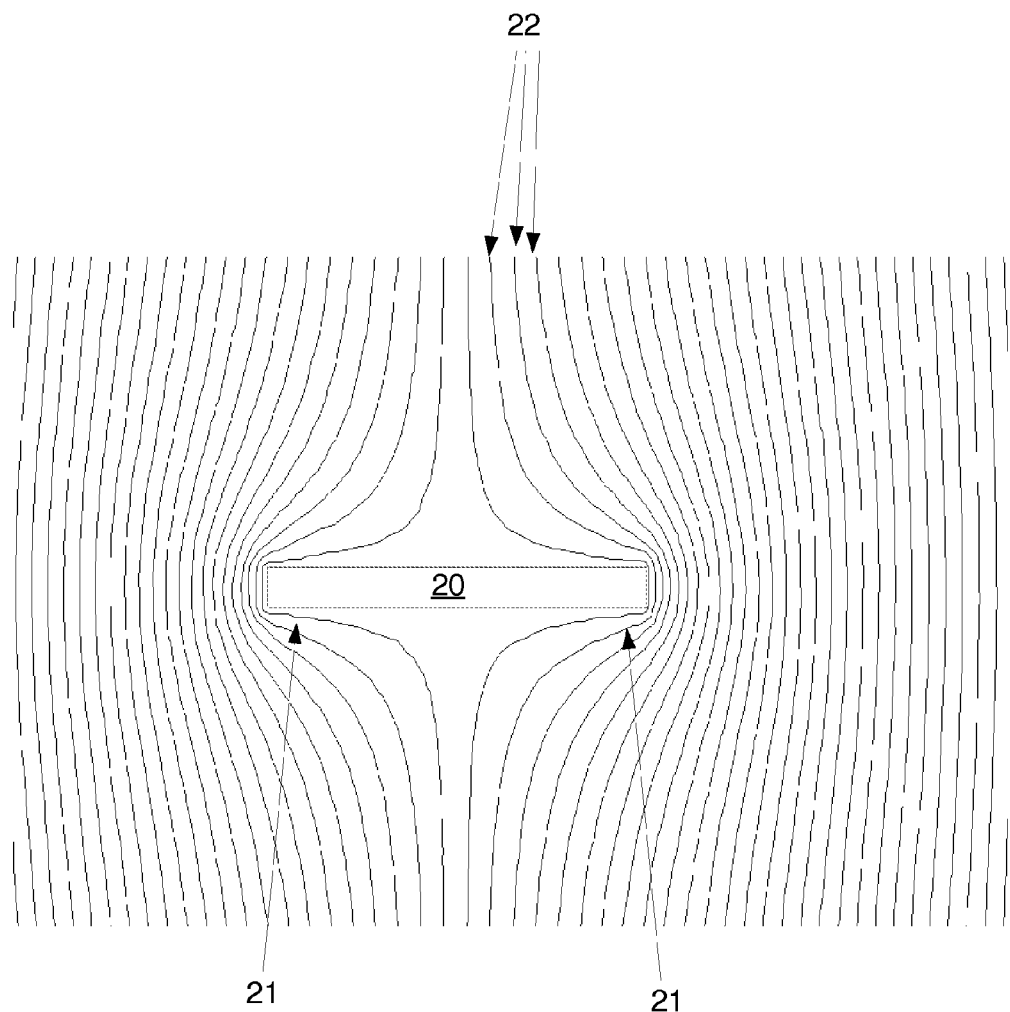
FIGS. 2a and 2b are diagrams of equipotential lines around a bar in an external electric field.

FIG. 2a is a diagram of equipotential lines around a bar of conductive material 20, such as a metal bar, in an external electric field. The metal bar 20 has two ends 21. The equipotential lines of the external electric field are indicated by the lines 22. FIG. 2 illustrates how the electric equipotential lines follow the contour of a conductive metal bar 20 in the external electric field. This results in high field strengths near the ends 21 of the wire, shown in FIG. 2 in that the equipotential lines are close to each other near the ends 21 of the metal bar. If the metal bar 20 is implanted in a weakly conductive medium, such as human tissue, for example the human brain, the distribution of equipotential lines leads to high current densities close to the ends 21 of the bare 20, because the current density is proportional to the electric field according to the law of Ohm.

Figure 2B:
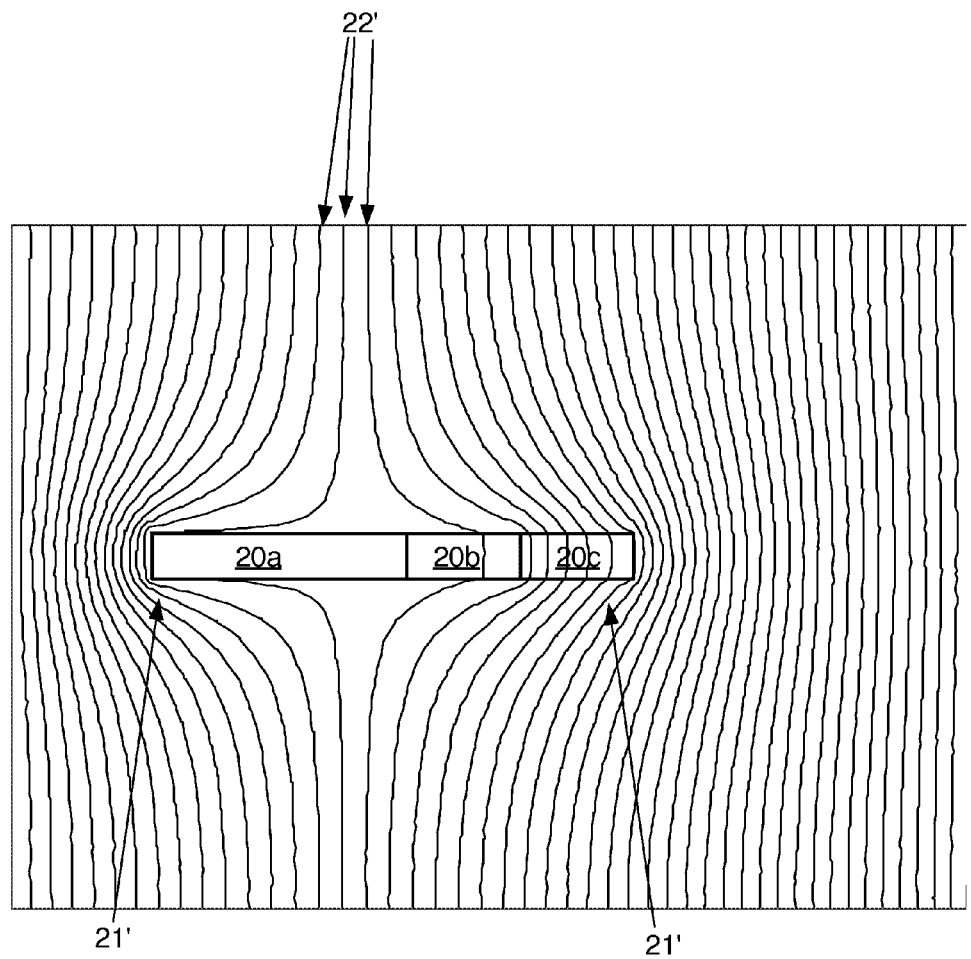

FIG. 2b is a diagram of equipotential lines around a bar in an external electric field. The metal bar has two ends 21'. The bar is divided into three regions 20a, 20b, and 20c with different conductivities. The equipotential lines of the external electric field are indicated by the lines 22 and FIG. 2b illustrates how the electric equipotential lines 22 follow the contour of a bar having three regions of different resistivity in the external electric field.

The region 20a is highly conductive and has low resistivity. The equipotential lines cannot enter such a material and are bent around its shape. Therefore, the density of the equipotential lines at the left-hand side of the region 20a is relatively high. This results in a high electric field strength at the left-hand side of the region 20a since the electric field strength is proportional to the density of the equipotential lines.

The region 20b has higher resistance than the region 20a, and the region 20c has much higher resistance than region 20a and higher resistance than 20b. This allows the equipotential lines to cross the region 20c. Because these equipotential lines are not bent around the right hand side of the region 20c, the resulting density of equipotential lines is much lower at the right hand side of the region 20c than at the left hand side of the region 20a. This results in a lower electric field strength at the right-hand side of the region 20c with high resistance compared to the left hand side of the bar having low resistance.

Figure 3:
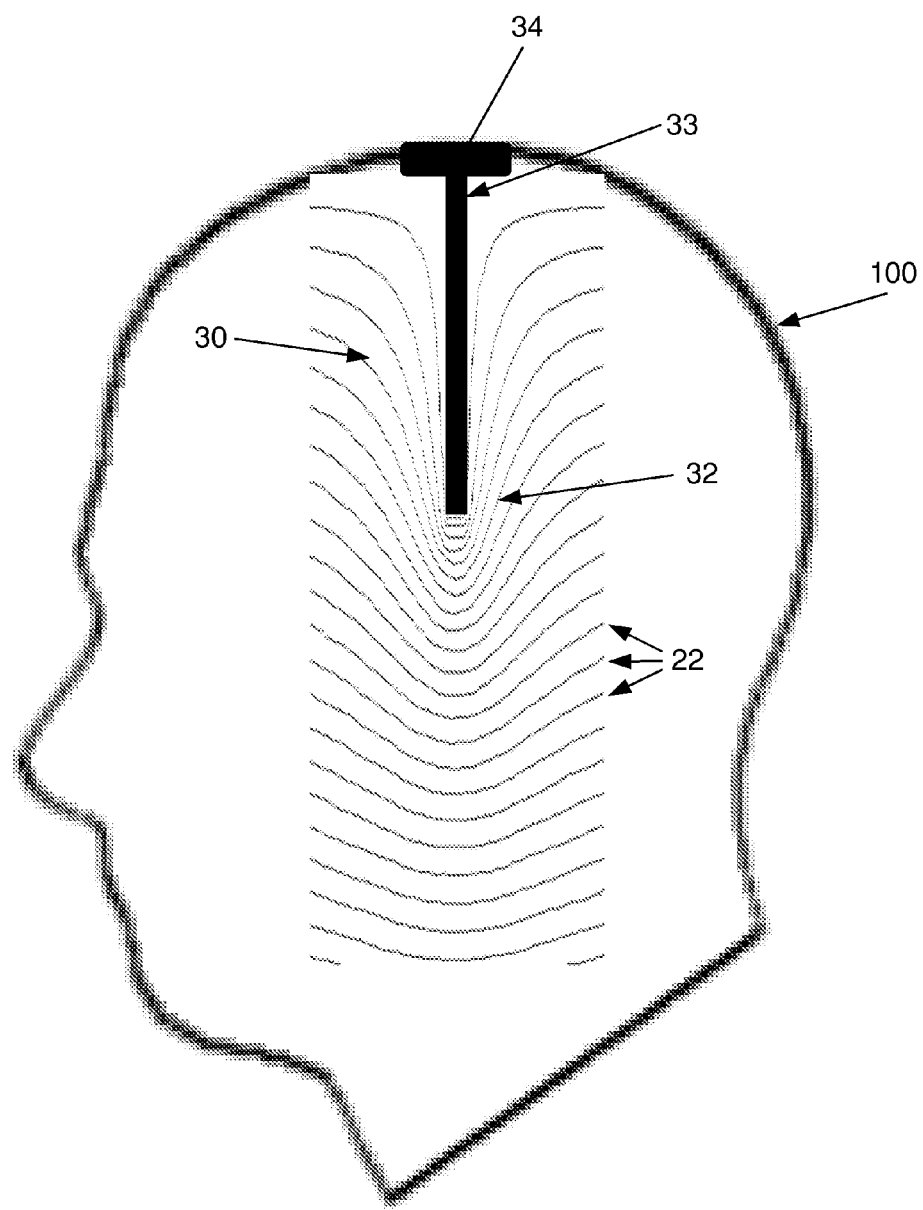
FIG. 3 is a diagrammatic drawing of a medical device with a probe implanted in the skull of a human patient.
Figure 4:
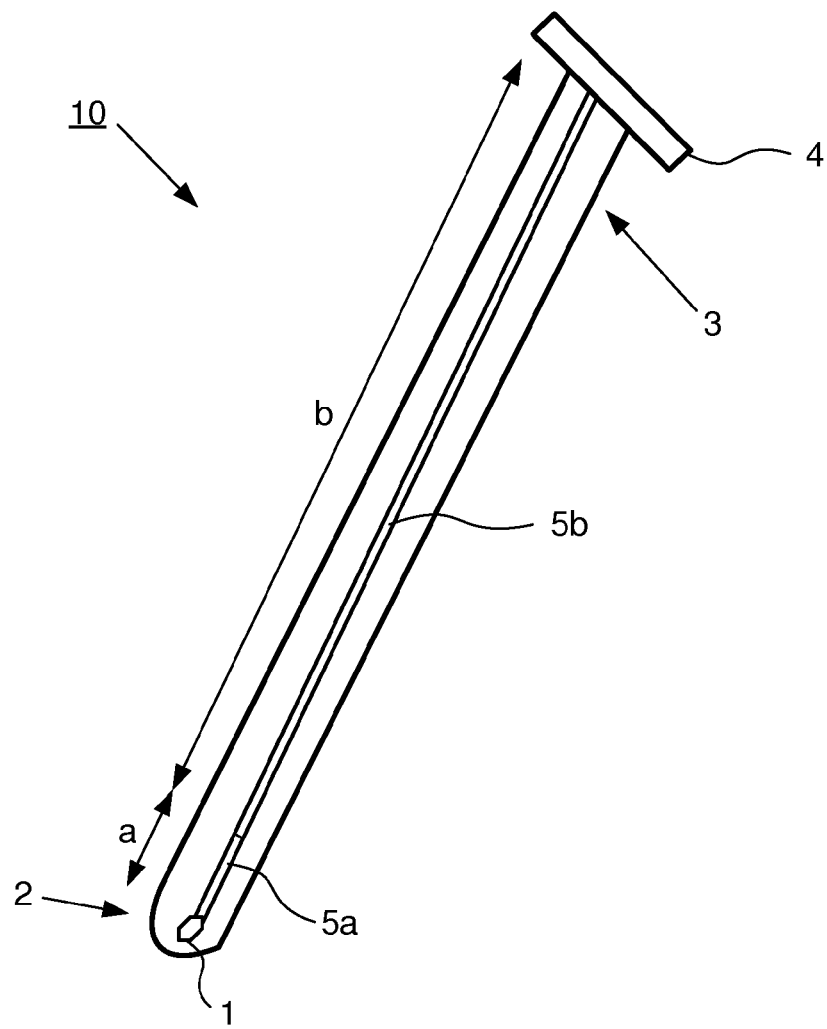
FIG. 4 is a cross section of a probe according to the invention for implantable electro-stimulation devices.

FIG. 3 is a diagrammatic drawing of a medical device with a probe 30 implanted in the skull 100 of a human patient. The probe 30 has a distal end 32 and a proximal end 33, the proximal end 33 being connected to a chamber 34 of the medical device. In the case of FIG. 4 the patient is subjected to an external electric field, whereof some equipotential lines are indicated. From FIG. 3 is clear that the equipotential lines close to the distal end 32 of the probe 30 are quite close, corresponding to a relatively high current density close to the distal end 32. It is noted, that the probe 30 in FIG. 3 is not a probe according to the invention; such a probe would render an altered configuration of the equipotential lines.

FIG. 4 shows an embodiment of a probe 10 of an electro-stimulation device according to the invention. The probe 10 has a distal end 2 and a proximal end 3. For the sake of clarity, FIG. 2 only discloses one electrode 1 in the probe 10, the electrode 1 being situated close to the distal 2 end of the probe. However, more than one electrode 1 would typically be advantageous in order to provide high resolution stimulation, more than one electrode is advantageous. The first section 5a extends from the electrode along the length of the probe to the second section 5b; the second section 5b of the wire extends from the interface with the first section 5a to the proximal end 3 of the probe, whereby the wire 5b may be connected to electronics within the chamber 4. According to the invention, the first section 5a has a first resistivity and the second section 5b has a second resistivity, where the first and second resistivities are different.

In an aspect of the invention, the resistivity of the first section 5a is higher than the resistivity at the second section 5b, so that the resistivity of the wire is higher close to the electrode compared to the rest of the wire.

In one embodiment of the probe, the first section 5a is made of material of a first resistivity and the second section 5b is made of material of a second resistivity, where the first resistivity is higher than the second resistivity. Hereby, the different resistivities of the wire are obtained by choosing different materials for the different sections of the wire. Alternatively or concurrently, wherein the first section 5a of the wire has a first sectional area and the second section 5b of the wire has a second sectional area, where the first sectional area is smaller than the second sectional area. Different sectional areas of the first and second sections provide different resistivities of the wire, since the resistivity $\rho$ of a resistive material is defined as $\rho = R \cdot l / A$, where R is the static resistivity of the material, A is the cross-sectional area of the piece of material and l is the length of the piece of material.

From FIG. 4 it is apparent, that the second section 5b of the wire is longer than the first section 5a of the wire. In FIG. 4, the length of the first section 5a is indicated by a, and the length of the second section 5b is indicated by b. Typically, the first section of wire constitutes between 2% and 40%, preferably between 5% and 20%, more preferably between 10% and 15% of the length of the wire. Thus, a may constitute 2-40%, preferably 5-20%, more preferably 10-15% of the total length a+b of the wire.

Moreover, the resistivity of the first section 5a may advantageously be two to 10 times higher than the resistivity of the second section 5b. For example, the first section 5a of the wire is of polysilicon material and the second section 5b of the wire is of metallic material.

Even though the wire shown in FIG. 4 has only two sections 5a, 5b, it is conceivable that the wire comprises more than two different sections, where each section has a resistivity different from other sections of the wire. Alternatively, the resistivity of the wire may change continuously along the length of the wire.

Even though only one electrode 1 is shown in FIG. 4, it is understood that typically the probe 10 comprises a plurality of electrode, such as 64 electrodes, each connected with a wire to the proximal end 3 of the probe 10 and to the chamber 4 of the medical device.

In short, the invention relates to a probe 10 for an implantable medical device. The probe has a distal end 2 and a proximal end 3, and the probe 10 moreover comprises an electrode 1 at the distal end. The electrode is connected to a wire 5 extending from the electrode to the proximal end of the probe, where the resistivity of the wire is non-uniform along the length of the wire. The wire may have high resistivity at the distal end of the probe and low resistivity wires elsewhere. The high resistivity wires reduce the peak current density in the tissue of an implanted device, and thus prevents destructive heating and/or undesired stimulation of tissue during MRI examination. This highly contributes to MR safety which is a highly desired feature for these implantable electrical stimulation devices.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A probe for an implantable medical device comprising:
   a distal end;
   a proximal end; and
   an electrode proximal to the distal end, the electrode connected to a wire having a length extending from the electrode to the proximal end of the probe,
   wherein the resistivity of the wire is non-uniform along the length of the wire, and
   wherein the resistivity of each portion of the wire along the length of the wire is different from the resistivity of adjacent portions of the wire.

2. A probe according to claim 1, wherein the wire comprises a first section and a second section, the first section of the wire being contiguous to the electrode.

3. A probe according to claim 2, wherein the first section is made of a first material and the second section is made of a second material, where the first material has a higher resistivity than the second material.

4. A probe according to claim 3, wherein the second section of the wire is longer than the first section of the wire.

5. A probe according to claim 3, wherein the first section of the wire constitutes between 2% and 40% of the wire.

6. A probe according to claim 3, wherein the first section of the wire constitutes between 5% and 20% of the wire.

7. A probe according to claim 3, wherein the first section of the wire constitutes between 10% and 15% of the wire.

8. A probe according to claim 2, wherein the first section of the wire has a first sectional area and the second section of the wire has a second sectional area, where the first sectional area is smaller than the second sectional area.

9. A probe according to claim 2, wherein the first section of the wire is of polysilicon material and the second section of the wire is of metallic material.

10. An implantable medical device comprising a probe according to claim 1.

11. A probe according to claim 1, wherein the resistivity of the wire monotonously increases along the length of the wire.

12. A probe according to claim 1, wherein the resistivity of the wire linearly increases along the length of the wire.

13. A probe according to claim 1, wherein the resistivity of the wire increases continuously along the length of the wire from the proximal end to the distal end.

* * * * *